United States Patent
Macho et al.

(10) Patent No.: US 10,004,893 B2
(45) Date of Patent: *Jun. 26, 2018

(54) WEARABLE DEFIBRILLATOR WITH AUDIO INPUT/OUTPUT

(71) Applicant: ZOLL Medical Corporation, Chelmsford, MA (US)

(72) Inventors: John D Macho, Farmington, PA (US); Shane S Volpe, Saltsburg, PA (US); Richard A Rattanni, Verona, PA (US); Philip C Skalos, Munhall, PA (US); Thomas E Kaib, Irwin, PA (US); Marshal W Linder, New Kensington, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/468,196

(22) Filed: Mar. 24, 2017

(65) Prior Publication Data

US 2017/0189672 A1 Jul. 6, 2017

Related U.S. Application Data

(60) Continuation of application No. 15/285,295, filed on Oct. 4, 2016, which is a continuation of application
(Continued)

(51) Int. Cl.
*A61N 1/00* (2006.01)
*A61N 1/04* (2006.01)
(Continued)

(52) U.S. Cl.
CPC .......... *A61N 1/0484* (2013.01); *A61B 5/0002* (2013.01); *A61B 5/0402* (2013.01);
(Continued)

(58) Field of Classification Search
USPC ............................................................. 607/4
See application file for complete search history.

(56) References Cited

U.S. PATENT DOCUMENTS 2,688,752 A 9/1954 Sbarra et al.
3,241,556 A 3/1966 Zacouto
(Continued)

FOREIGN PATENT DOCUMENTS

EP 396048 A1 11/1990
EP 0295497 B1 9/1993
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.
(Continued)

*Primary Examiner* — Nicole F Johnson
(74) *Attorney, Agent, or Firm* — ZOLL Medical Corporation

(57) ABSTRACT

A wearable device and method of monitoring the condition of a patient. The wearable device includes at least one sensor and at least one processor operatively connected to the at least one sensor. The wearable device also includes an operator interface device operatively connected to the at least one processor. The at least one processor causes the device to allow for customization of at least one output message to be delivered via the operator interface device.

29 Claims, 2 Drawing Sheets

Related U.S. Application Data

No. 14/607,843, filed on Jan. 28, 2015, now Pat. No. 9,492,676, which is a continuation of application No. 14/325,041, filed on Jul. 7, 2014, now Pat. No. 8,965,500, which is a division of application No. 13/757,105, filed on Feb. 1, 2013, now Pat. No. 8,774,917, which is a continuation of application No. 12/082,168, filed on Apr. 9, 2008, now Pat. No. 8,369,944.

(60) Provisional application No. 60/933,310, filed on Jun. 6, 2007.

(51) Int. Cl.
| | | |
|---|---|---|
| *A61N 1/39* | (2006.01) | |
| *A61B 5/0408* | (2006.01) | |
| *A61N 1/372* | (2006.01) | |
| *A61B 5/00* | (2006.01) | |
| *A61B 5/0402* | (2006.01) | |

(52) U.S. Cl.
CPC .......... *A61B 5/04085* (2013.01); *A61N 1/046* (2013.01); *A61N 1/37217* (2013.01); *A61N 1/3925* (2013.01); *A61N 1/3993* (2013.01)

(56) References Cited

U.S. PATENT DOCUMENTS

| | | |
|---|---|---|
| 3,409,007 A | 11/1968 | Fuller |
| 3,460,542 A | 8/1969 | Gemmer |
| 3,553,651 A | 1/1971 | Bird et al. |
| 3,664,560 A | 5/1972 | Perkins |
| 3,702,613 A | 11/1972 | Panico et al. |
| 3,706,313 A | 12/1972 | Milani et al. |
| 3,724,455 A | 4/1973 | Unger |
| 3,744,482 A | 7/1973 | Kaufman et al. |
| 3,826,245 A | 7/1974 | Funfstuck |
| 3,862,636 A | 1/1975 | Bell et al. |
| 3,886,950 A | 6/1975 | Ukkestad et al. |
| 3,897,785 A | 8/1975 | Barto, Jr. |
| 3,942,533 A | 3/1976 | Cannon, III |
| 3,961,623 A | 6/1976 | Milani et al. |
| 4,002,239 A | 1/1977 | Buchalter |
| 4,058,127 A | 11/1977 | Buchalter |
| 4,088,138 A | 5/1978 | Diack et al. |
| 4,094,310 A | 6/1978 | McEachern et al. |
| 4,136,690 A | 1/1979 | Anderson et al. |
| 4,576,170 A | 3/1986 | Bradley et al. |
| 4,580,572 A | 4/1986 | Granek et al. |
| 4,583,547 A | 4/1986 | Granek et al. |
| 4,608,987 A | 9/1986 | Mills |
| 4,619,265 A | 10/1986 | Morgan et al. |
| 4,632,122 A | 12/1986 | Johansson et al. |
| 4,679,572 A | 7/1987 | Baker, Jr. |
| 4,698,848 A | 10/1987 | Buckley |
| 4,729,377 A | 3/1988 | Granek et al. |
| 4,823,796 A | 4/1989 | Benson |
| 4,889,131 A | 12/1989 | Salem et al. |
| 4,926,879 A | 5/1990 | Sevrain et al. |
| 4,928,690 A | 5/1990 | Heilman et al. |
| 4,938,231 A | 7/1990 | Milijasevic et al. |
| 4,978,926 A | 12/1990 | Zerod et al. |
| 4,991,217 A | 2/1991 | Garrett et al. |
| 5,000,189 A | 3/1991 | Throne et al. |
| 5,007,427 A | 4/1991 | Suzuki et al. |
| 5,062,834 A | 11/1991 | Gross et al. |
| 5,078,134 A | 1/1992 | Heilman et al. |
| 5,097,830 A | 3/1992 | Eikefjord et al. |
| 5,224,479 A | 7/1993 | Sekine |
| 5,225,763 A | 7/1993 | Krohn et al. |
| 5,306,956 A | 4/1994 | Ikeda et al. |
| 5,333,616 A | 8/1994 | Mills et al. |
| 5,342,404 A | 8/1994 | Alt et al. |
| 5,348,008 A | 9/1994 | Bornn et al. |
| 5,357,696 A | 10/1994 | Gray et al. |
| 5,361,412 A | 11/1994 | Perry |
| 5,365,932 A | 11/1994 | Greenhut |
| 5,371,692 A | 12/1994 | Draeger et al. |
| 5,381,798 A | 1/1995 | Burrows |
| 5,405,361 A | 4/1995 | Persson |
| 5,413,262 A | 5/1995 | Dewire et al. |
| 5,433,737 A | 7/1995 | Aimone |
| 5,443,494 A | 8/1995 | Paolizzi et al. |
| 5,470,341 A | 11/1995 | Kuehn et al. |
| 5,472,453 A | 12/1995 | Alt |
| 5,544,661 A | 8/1996 | Davis et al. |
| 5,558,640 A | 9/1996 | Pfeiler et al. |
| 5,601,612 A | 2/1997 | Gliner et al. |
| 5,606,242 A | 2/1997 | Hull et al. |
| 5,607,454 A | 3/1997 | Cameron et al. |
| 5,611,085 A | 3/1997 | Rasmussen |
| 5,619,117 A | 4/1997 | Koenck |
| 5,620,470 A | 4/1997 | Gliner et al. |
| 5,625,291 A | 4/1997 | Brink et al. |
| 5,662,689 A | 9/1997 | Elsberry et al. |
| 5,701,894 A | 12/1997 | Cherry et al. |
| 5,708,978 A | 1/1998 | Johnsrud |
| 5,718,242 A | 2/1998 | McClure et al. |
| 5,721,482 A | 2/1998 | Benvegar et al. |
| 5,724,025 A | 3/1998 | Tavori |
| 5,730,143 A | 3/1998 | Schwarzberg |
| 5,738,102 A | 4/1998 | Lemelson |
| 5,741,306 A | 4/1998 | Glegyak et al. |
| 5,758,366 A | 6/1998 | Wilson |
| 5,758,443 A | 6/1998 | Pedrazzini |
| 5,772,604 A | 6/1998 | Langberg et al. |
| 5,792,190 A | 8/1998 | Olson et al. |
| 5,824,017 A | 10/1998 | Sullivan et al. |
| 5,827,196 A | 10/1998 | Yeo et al. |
| 5,830,236 A | 11/1998 | Mouchawar et al. |
| 5,833,714 A | 11/1998 | Loeb |
| 5,887,978 A | 3/1999 | Lunghofer et al. |
| 5,924,979 A | 7/1999 | Swedlow et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,047,203 A | 4/2000 | Sackner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,208,896 B1 | 3/2001 | Mulhauser |
| 6,253,099 B1 | 6/2001 | Oskin et al. |
| 6,280,461 B1 | 8/2001 | Glegyak et al. |
| 6,336,900 B1 | 1/2002 | Alleckson et al. |
| 6,390,996 B1 | 5/2002 | Halperin et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,681,003 B2 | 1/2004 | Linder et al. |
| 6,687,523 B1 | 2/2004 | Jayaramen et al. |
| 6,690,969 B2 | 2/2004 | Bystrom et al. |
| 6,694,191 B2 | 2/2004 | Starkweather et al. |
| 6,736,759 B1 * | 5/2004 | Stubbs .................. A63B 22/00 482/5 |
| 6,804,554 B2 | 10/2004 | Ujhelyi et al. |
| 6,827,695 B2 | 12/2004 | Palazzolo et al. |
| 6,889,078 B2 | 5/2005 | Struble et al. |
| 6,889,079 B2 | 5/2005 | Bocek et al. |
| 6,908,437 B2 | 6/2005 | Bardy |
| 6,944,498 B2 | 9/2005 | Owen et al. |
| 6,961,612 B2 | 11/2005 | Elghazzawi et al. |
| 6,990,373 B2 | 1/2006 | Jayne et al. |
| 7,130,690 B2 | 10/2006 | Rueter et al. |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,712,373 B2 | 5/2010 | Nagle et al. |

(56) References Cited

U.S. PATENT DOCUMENTS

| | | |
|---|---|---|
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,406,842 B2 | 3/2013 | Kaib et al. |
| 8,774,917 B2 | 7/2014 | Macho et al. |
| 8,965,500 B2 | 2/2015 | Macho et al. |
| 2001/0031991 A1 | 10/2001 | Russial |
| 2002/0077689 A1 | 6/2002 | Kirkland |
| 2003/0004547 A1 | 1/2003 | Owen et al. |
| 2003/0032988 A1 | 2/2003 | Fincke |
| 2003/0055460 A1 | 3/2003 | Owen et al. |
| 2003/0095648 A1 | 5/2003 | Kaib et al. |
| 2003/0109904 A1 | 6/2003 | Silver et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2003/0216786 A1 | 11/2003 | Russial |
| 2004/0007970 A1 | 1/2004 | Ma et al. |
| 2004/0049233 A1 | 3/2004 | Edwards |
| 2004/0143297 A1 | 7/2004 | Ramsey |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0131465 A1 | 6/2005 | Freeman et al. |
| 2005/0144043 A1 | 6/2005 | Holland et al. |
| 2005/0246199 A1 | 11/2005 | Futch |
| 2005/0283198 A1 | 12/2005 | Haubrich et al. |
| 2006/0036292 A1 | 2/2006 | Smith et al. |
| 2006/0085049 A1 | 4/2006 | Cory et al. |
| 2006/0095091 A1 | 5/2006 | Drew |
| 2006/0178706 A1 | 8/2006 | Lisogurski et al. |
| 2006/0211934 A1 | 9/2006 | Hassonjee et al. |
| 2006/0220809 A1 | 10/2006 | Stigall et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0143864 A1 | 6/2007 | Cabana et al. |
| 2007/0161913 A1 | 7/2007 | Farrell et al. |
| 2007/0162390 A1 | 7/2007 | Pancholy et al. |
| 2007/0169364 A1 | 7/2007 | Townsend et al. |
| 2007/0197878 A1 | 8/2007 | Shklarski |
| 2007/0239214 A1 | 10/2007 | Cinbis |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0030656 A1 | 2/2008 | Watson et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0097793 A1 | 4/2008 | Dicks et al. |
| 2008/0103402 A1 | 5/2008 | Stickney et al. |
| 2008/0167535 A1 | 7/2008 | Stivoric et al. |
| 2008/0177341 A1 | 7/2008 | Bowers |
| 2008/0183090 A1 | 7/2008 | Farringdon et al. |
| 2008/0249591 A1 | 10/2008 | Gaw et al. |
| 2008/0287749 A1 | 11/2008 | Reuter |
| 2008/0294019 A1 | 11/2008 | Tran |
| 2008/0306560 A1 | 12/2008 | Macho et al. |
| 2008/0312520 A1 | 12/2008 | Rowlandson et al. |
| 2008/0312522 A1 | 12/2008 | Rowlandson et al. |
| 2008/0312709 A1 | 12/2008 | Volpe et al. |
| 2009/0018428 A1 | 1/2009 | Dias et al. |
| 2009/0066366 A1 | 3/2009 | Solomon |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0118808 A1 | 5/2009 | Belacazar et al. |
| 2009/0138059 A1 | 5/2009 | Ouwerkerk |
| 2009/0146822 A1 | 6/2009 | Soliman |
| 2009/0212984 A1 | 8/2009 | Baker |
| 2009/0231124 A1 | 9/2009 | Klabunde et al. |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2010/0010559 A1 | 1/2010 | Zhang et al. |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0081962 A1 | 4/2010 | Hamaguchi et al. |
| 2010/0114243 A1 | 5/2010 | Nowak et al. |
| 2010/0171611 A1 | 7/2010 | Gao et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0015533 A1 | 1/2011 | Cox et al. |
| 2011/0022105 A9 | 1/2011 | Owen et al. |
| 2011/0093840 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0016361 A1 | 1/2012 | White et al. |
| 2012/0053479 A1 | 3/2012 | Hopenfeld |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0197353 A1 | 8/2012 | Donnelly et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2013/0013014 A1 | 1/2013 | Donnelly et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2015/0148857 A1 | 5/2015 | Macho et al. |

FOREIGN PATENT DOCUMENTS

| | | |
|---|---|---|
| EP | 0335356 B1 | 3/1996 |
| EP | 0707825 A2 | 4/1996 |
| EP | 0761255 A1 | 3/1997 |
| EP | 1455640 B1 | 1/2008 |
| EP | 1720446 B1 | 7/2010 |
| JP | 5115450 A | 5/1993 |

(56) References Cited

FOREIGN PATENT DOCUMENTS

| | | |
|---|---|---|
| JP | 2002200059 A | 7/2002 |
| WO | 199722297 A1 | 6/1997 |
| WO | 199839061 A2 | 9/1998 |
| WO | 199843537 A1 | 10/1998 |
| WO | 199959465 A1 | 11/1999 |
| WO | 200002484 A1 | 1/2000 |
| WO | 200030529 A1 | 6/2000 |
| WO | 2004054656 A1 | 7/2004 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2010025432 A1 | 3/2010 |
| WO | 2010077997 A2 | 7/2010 |

OTHER PUBLICATIONS

DeBock, et al., "Captopril treatment of chronic heart failure in the very old," J. Gerontol. (1994) 49: M148-M152.

Herlihy et al. The Art of Multiple Processor Programming. Chapter 1, p. 1. Mar. 3, 2008.

http://web.archive.org/web/20030427001846/http:/www.lifecor.com/imagelib/imageproduct.asp. Published by LifeCor, Inc., 2002, on a webpage owned by LifeCor, Inc.

O'Keeffe et al., "Reproducability and responsiveness of quality of life assessment and six minute walk test in elderly heart failure patients," Heart (1998) 80: 377-382.

Wikipedia, Multi-core processor, Dec. 11, 2009, http://web.archive.org/web/20091211134408/http://en.wikipedia.org/wiki/Multicore_processor#Hardware.

* cited by examiner

WEARABLE DEFIBRILLATOR WITH AUDIO INPUT/OUTPUT

CROSS-REFERENCE TO RELATED APPLICATIONS

This application is a continuation of U.S. application Ser. No. 15/285,295, titled "Wearable Defibrillator with Audio Input/Output" filed on Oct. 4, 2016, which is a continuation of U.S. application Ser. No. 14/607,843, titled "Wearable Defibrillator with Audio Input/Output" filed on Jan. 28, 2015, now U.S. Pat. No. 9,492,676, which is a continuation of U.S. application Ser. No. 14/325,041 titled "Wearable Defibrillator with Audio Input/Output" filed on Jul. 7, 2014, now U.S. Pat. No. 8,965,500, which is a division of U.S. application Ser. No. 13/757,105 titled "Wearable Defibrillator with Audio Input/Output" filed on Feb. 1, 2013, now U.S. Pat. No. 8,774,917, which is a continuation of U.S. application Ser. No. 12/082,168 titled "Wearable Defibrillator with Audio Input/Output" filed Apr. 9, 2008, now U.S. Pat. No. 8,369,944, which claims priority under 35 U.S.C. § 119(e) to U.S. Provisional Patent Application Ser. No. 60/933,310 filed on Jun. 6, 2007. Each of the above foregoing applications are hereby incorporated herein by reference in their entirety.

FIELD OF THE INVENTION

This invention relates to wearable defibrillators.

BACKGROUND

There are many patients susceptible to heart arrhythmias who are at risk sudden death. For example, patients undergoing a coronary artery occlusion and myocardial infarction are at substantial risk of tachyarrhythmia for several weeks following the coronary artery occlusion. Such patients are generally hospitalized but can be discharged earlier if there is a practical means to protect them from life threatening arrhythmias. One such practical means includes the implantation of an automatic defibrillator. However, patients may also be discharged prior to such an implantation if an external defibrillator, such as, for example, a wearable defibrillator, is available in case they experience a life-threatening tachyarrhythmia.

There are also patients who are placed at an inordinate risk due to the surgery required for implanting an implantable defibrillator. For such patients, implantation would preferably be avoided so such an inordinate risk could be avoided or otherwise mitigated.

Wearable defibrillators are often used to help people who have an increased risk of experiencing a life threatening arrhythmia due to specific heart conditions. Such wearable defibrillators are typically configured to provide treatment if a life threatening arrhythmia is detected. For example, U.S. Pat. Nos. 4,928,690, 5,078,134, 5,741,306, 5,944,669, 6,065,154, 6,097,987, 6,253,099, 6,280,461 and 6,681,003, disclose wearable defibrillators. The entirety of U.S. Pat. Nos. 4,928,690, 5,078,134, 5,741,306, 5,944,669, 6,065, 154, 6,097,987, 6,253,099, 6,280,461 and 6,681,003, are hereby incorporated herein by reference.

Wearable defibrillators are typically used to help patients that either cannot risk an implantation of a defibrillator or are awaiting such an implantation. Occasionally, analysis performed by the wearable defibrillator may falsely indicate that the patient is experiencing an arrhythmia that requires treatment. In such circumstances, the wearable defibrillator generates an audible alarm that is configured to stop if a patient provides a required response, such as, for example, pressing one or more response buttons. If a patient fails to press such buttons or otherwise provide a required response, the device may assume the patient is unconscious and is experiencing a condition requiring treatment. Occasionally, a bystander who is unfamiliar with a wearable defibrillator may interfere with the device by intentionally pressing the response buttons or otherwise providing a response which delays or inhibits patient treatment.

The present invention is directed toward overcoming one or more of the above-mentioned problems.

SUMMARY

A wearable defibrillator is provided that includes one or more therapy pads one or more sensors, one or more processing units operatively connected to the one or more therapy pads and one or more sensors and one or more audio devices operatively connected to the one or more processing units. The one or more audio devices are configured to receive audio input from a patient.

One embodiment of the wearable defibrillator may include one or more audio devices that are one or more microphones, one or more speakers or a combination of one or more speakers and one or more microphones. Another embodiment of the wearable defibrillator may include one or more processing units that include one or more processors and at least one memory connected to the one or more processors.

In another embodiment of the wearable defibrillator, the one or more processing units can be configured to record the patient name using a microphone and store the audio recording in non volatile memory. In some embodiments of the wearable defibrillator, a recording of the patient's name made during setup by either an operator or patient can be played back during startup to uniquely identify who the wearable defibrillator belongs to.

In some embodiments of the wearable defibrillator, the one or more processing units can be configured to cause at least one patient responsiveness test to be run upon detection of an arrhythmia condition by the one or more sensors. In one embodiment, one of the one or more responsiveness tests can include at least one voice recognition responsiveness test, at least one button responsiveness test, or any combination thereof. For example, the one or more processing units can be configured to cause a response button responsiveness test to be run only after a voice recognition responsiveness test resulted in a response that indicated the patient is not conscious. Of course, other embodiments of the wearable defibrillator may include one or more processing units that are configured to run other patient responsiveness tests or sequences of such patient responsiveness tests.

In one embodiment of the wearable defibrillator, the audio input can include one or more sounds, such as, for example, at least one spoken word, made by the patient and the one or more processing units can be configured to recognize the audio input from the patient. In some embodiments of the wearable defibrillator, the one or more processing units may be configured such that the wearable defibrillator either delays or does not provide a treatment to the patient when the one or more sounds is received by the one or more audio devices and recognized by the one or more processing units.

In another embodiment of the wearable defibrillator, the wearable defibrillator may include one or more processing units that are configured to recognize audio input provided by a base unit configured to operatively connect to the wearable defibrillator to verify that the base unit is functioning properly. In some embodiments of the wearable defibrillator, the base unit can include a modem and the audio input provided by the base unit can include sound made by the modem.

In yet another embodiment of the wearable defibrillator, the wearable defibrillator can include one or more mechanisms connected to the one or more processing units and the one or more processing units are configured to recognize input provided by the one or more mechanisms to verify that the one or more mechanisms are operating correctly. In some embodiments of the wearable defibrillator, the one or more mechanisms can include relays, switches or any combination thereof that produce an audible sound upon activation or deactivation.

In one embodiment of the wearable defibrillator, the processing unit of a wearable defibrillator can be configured to cause an alarm to be emitted to verify that the wearable defibrillator can properly emit the alarm. In another embodiment, the one or more processing units can be configured to cause one or more speakers to produce audio output and be configured to adjust at least one of the frequency and the amplitude characteristics of the audio output based upon audio input received from one or more microphones.

In some embodiments of the wearable defibrillator, the one or more processing units can be configured to cause data obtained by the one or more sensors to be recorded in memory connected to the one or more processing units. In one embodiment of the wearable defibrillator, the audio input can include a command and the one or more processing units can be configured to cause data obtained by the one or more sensors to be recorded in at least one memory after the command is received by the one or more audio devices.

In one embodiment of the wearable defibrillator, the one or more processing units can be configured to cause a self-diagnostic test to be run if the audio input includes a high amplitude and short duration noise that may be indicative of device abuse.

A system configured to monitor a patient is also provided. The system includes a central location, and a wearable defibrillator configured to operatively connect to the central location. The wearable defibrillator includes one or more therapy pads, one or more sensors, one or more processing units operatively connected to the one or more therapy pads and one or more sensors and one or more audio devices operatively connected to the one or more processing units. The one or more audio devices are configured to receive audio input from a patient.

In some embodiments, the system may further include a base station configured to operatively connect the wearable defibrillator to the central location. In other embodiments, the one or more processing units of the wearable defibrillator may include at least one communication device configured to connect the wearable defibrillator to the central location. Preferably, the one or more communication devices include a modem, a network card, one or more networking programs, other networking mechanisms or any combination thereof.

In one embodiment of the system, the one or more audio devices can be a microphone. In another embodiment of the system, the base station can be configured to communicate with the central location and the wearable defibrillator may be configured to transmit data from the wearable defibrillator to the central location. In yet another embodiment of the system, the central location can include one or more memory and be configured to store data transmitted from the wearable defibrillator in the one or more memory.

A method of providing treatment to a patient is also provided. The method can include providing a wearable defibrillator to the patient that includes one or more audio devices, monitoring the condition of the patient, providing audio output from the one or more audio devices to the patient to verify a monitored arrhythmia condition exists, receiving audio input from the patient with the one or more audio devices and providing treatment to the patient based on the audio input received from the patient. It should be appreciated that the audio input received from the patient may include silence or may include audible responses.

In some embodiments of the method of providing treatment to a patient, the method may also include recording the condition of the patient and communicating the recorded condition of the patient to a central location. In other embodiments of the method, the method may include utilizing one or more of the audio devices to conduct at least one diagnostic test of the wearable defibrillator, recording the results from the one or more diagnostic tests and evaluating the results of the test or tests.

Other details, objects, and advantages of the invention will become apparent as the following description of certain present preferred embodiments thereof and certain present preferred methods of practicing the same proceeds.

BRIEF DESCRIPTION OF THE DRAWINGS

Present preferred embodiments of the invention are shown in the accompanying drawings and certain present preferred methods of practicing the same are also illustrated therein.

DETAILED DESCRIPTION

Figure 1:
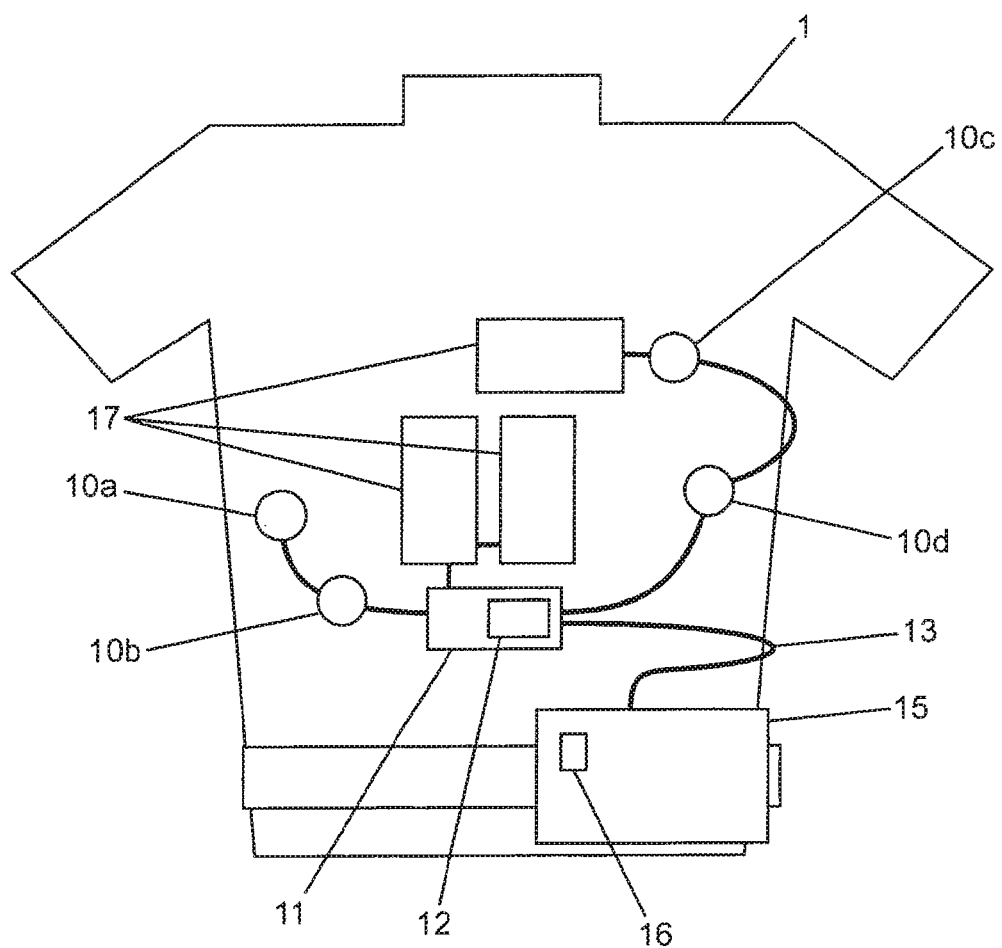
FIG. 1 is a schematic view of a first embodiment of the present invention, which illustrates an embodiment of a wearable defibrillator.

Referring to FIG. 1, a wearable defibrillator may be worn by a patient and may include a belt or harness or other apparel configured to permit the patient to wear the defibrillator. Sensors, such as electrodes 10a, 10b, 10c and 10d are removably attached to the patient when the wearable defibrillator is worn by the patient. The electrodes 10a, 10b, 10c and 10d form part of electrode assembly 11 and are operatively connected to a processing unit 15 via a trunk cable 13. In some embodiments, the processing unit 15 may include, without limitation, one or more processors, one or more controllers and/or one or more programs or other software stored in memory operatively connected to one or more processors.

The processing unit 15 is operatively connected to therapy pads 17, at least one tactile stimulator 12, electrode assembly 11, and one or more audio devices 16. The audio devices 16 may include, for example, a microphone and a speaker. The therapy pads 17 are removably connected to the patient when the defibrillator is worn. The processing unit 15 may include a visual read out and a speaker for communicating with the patient or others around the patient.

A trunk cable 13 may be used to connect the electrode assembly 11 to the processing unit 15 and audio devices 16. Of course, other types of cables or other connection devices used to operatively connect the electrode assembly 11 to the processing unit 15, speakers, microphones or other audio devices 16 may also be used. Wiring or other connection devices may also be used to connect at least one portion of the electrode assembly 11 to the electrodes 10*a*, 10*b*, 10*c*, and 10*d*. Of course, the processing unit 15 may alternatively be operatively connected to one or more of the electrodes 10*a*, 10*b*, 10*c*, 10*d*, therapy pads 17, electrode assembly 11, audio devices 16 and stimulator 12 by a wireless connection or a combination of wireless and wired connections.

The audio devices 16 preferably include a Knowles Acoustics WP-23502 microphone, a speaker and audio circuitry that include an audio CODEC and an audio amplifier. The audio CODEC may contain an interpolation filter and a noise shaper. An AC97 interface may be used to operatively connect the processing unit 15 and the one or more audio devices 16. Of course, other interfaces or other connection mechanisms known to those skilled in the art may also be used to operatively connect the processing unit 15 to the one or more audio devices 16.

At least one of the electrode assembly 11 and processing unit 15 have at least one processor that is configured to evaluate the cardiac condition of the patient and cause delivery of the appropriate treatment to the patient. The therapy pads 17 are configured to provide treatment, such as, for example, electric defibrillation, to the wearer after the processing unit 15 determines that such treatment should be delivered to the patient. The therapy pads 17 may include the application devices disclosed in U.S. Pat. No. 5,078,134, or other devices configured to provide treatment to the patient.

The processing unit 15 may display one or more visuals identifying the patient's condition or conditions based at least in part on one or more conditions sensed by the electrodes 10*a*, 10*b*, 10*c*, and 10*d*. A speaker may be an audio device 16 that is used to communicate with the patient or others located near the patient. The speaker or other audio device 16 may be housed within the processing unit 15 or be attached to the processing unit 15 or another portion of the wearable defibrillator such as, for example, the electrode assembly 11.

A microphone may also be an audio device 16 attached to the processing unit 15. The microphone may be configured to detect patient and environmental noise. One or more portions of the processing unit 15 can be operatively connected to, or otherwise incorporate, voice recognition software so the processing unit 15 can determine, based on whether or not it recognizes the voice of the wearer, whether an arrhythmia condition exists that warrants delivery of treatment or if such delivery should be delayed. The processing unit 15 may also be operatively connected to memory or another storage device that stores information such as, for example, the patient's voice signature so the processing unit 15 may identify a speaker's voice and determine when the patient is providing audio input.

The processing unit 15 may include one or more processors that are configured to use a confidence algorithm to determine when treatment should be delivered. The confidence algorithm may base arrhythmia detection on one or more inputs such as, but not limited to, data obtained from sensing electrodes 10*a*, 10*b*, 10*c* and 10*d*, one or more electrocardiograms. ("ECGs"), response button responsiveness test results, voice recognition responsiveness test results, etc. Preferably, the processing unit 15 is configured so that treatment is not delivered unless the confidence algorithm determines that there is a 100% confidence that the patient is experiencing a life threatening arrhythmia.

The one or more audio devices 16 may be configured to identify whether background noise exists. In the event no or little background noise is sensed, the confidence in the detection can be increased. The processing unit 15 may also be configured to permit the delivery of treatment to be accelerated if no background noise or little background noise is detected by the one or more audio devices 16.

The processing unit 15 may be configured to delay a delivery of treatment if a high level of background noise is identified because significant background noise may reduce the quality of the data obtained by the electrodes 10*a*, 10*b*, 10*c*, or 10*d*. For example, the quality of ECG sensing electrodes may be reduced with significant background noise possibly caused by patient motion and can result in false detection of a condition requiring treatment. If a high level of background noise is identified, the processing unit 15 can be configured to delay treatment so other tests or data can be obtained to verify that the patient requires treatment or to increase the audio output level of alarms used to warn any people surrounding the patient that treatment is about to be provided to the patient so that no one touches the patient during the application of the treatment.

The audio devices 16 may also be configured so that speaker volumes are increased whenever certain background noise levels are detected. Such increased volumes permit audio outputs to be heard by the patient or people near the patient when the patient is in a high noise environment. Such audio outputs may include alarms, instructions or communication related to patient responsiveness tests, which are discussed more fully below.

The processing unit 15 may be configured to cause a voice recognition responsiveness test to be run as part of determining that the patient is experiencing a condition requiring treatment. The voice responsiveness test may include an audio device 16, such as, for example, a speaker, to verbally ask the patient if the patient is conscious. In the event a microphone or other audio device 16 senses that the patient responds with a positive verbal comment, such as, for example, "yes", the processing unit 15 can be configured to delay treatment. In the event the patient does not provide an answer that is sensed by an audio device 16 or that such data is not provided to the processing unit 15, the processing unit 15 can be configured to cause a speaker to provide a verbal message asking the patient to press one or more buttons or activate one or more actuators connected to the defibrillator to verify the patient is conscious. The one or more buttons may be located on, in, or adjacent the belt, harness, vest, or monitor of the defibrillator.

In one embodiment, the processing unit 15 can be configured to cause the speaker to ask the patient certain questions in the event a possible condition is identified that may require delivery of a treatment. For example, the speaker may be configured to ask the patient "are you conscious?" or "if you are conscious, please state your name." The processing unit 15 can be operatively connected to memory or another storage device that contains the patient's voice signature to verify the patient is answering the questions. Such verification prevents a passerby from preventing treatment of the patient by improperly responding to the questions.

The use of audio devices 16, such as, for example, a microphone and a speaker, permit the patient to have real-time input provided to the defibrillator. The processing unit 15 may also be configured to record the audio input in the proximity of the wearable device for later review by emergency personnel. Such information may help care providers determine a diagnosis for the patient or treat the patient.

The one or more audio devices may also be operatively connected to the processing unit 15 such that the processing unit 15 can cause the patient's conditions being sensed by electrodes 10*a*, 10*b*, 10*c*, or 10*d* to be recorded and stored. Such recording and storage can be actuated by verbal commands issued by the patient that are received by the audio device 16, such as, for example, a microphone, or by the actuation of an actuator such as, for example, a button operatively connected to the processing unit 15. The processing unit 15 can also be configured so the audio device 16, such as, for example, a microphone, records a message provided by the patient that explains how he feels and why he initiated the recording of the conditions being sensed by one or more of the electrodes 10*a*, 10*b*, 10*c*, and 10*d*. The recorded audio and sensed information may be stored in memory operatively connected to the processing unit 15 or be transmitted to a central location and/or to health care providers. Transmissions to a central location are discussed more fully below. Such recordings may permit a health care provider or doctor to formulate a diagnosis based on the sensed conditions or otherwise act on such information to provide services the recorded conditions indicate the patient needs.

In the event the patient has difficulty with an aspect of the defibrillator, the processing unit 15 can be configured so a speaker or other audio device provides the patient with certain verbal instructions. The instructions may also be provided in specific situations where the patient has difficulty understanding instructions or the processing unit 15 is not receiving any expected input from the patient. Special messaging instructions can be recorded during patient setup to support the personal communication needs of the patient or may be operatively connected to the processing unit 15 such that the instructions may be provided to the patient during the setup of the defibrillator in the event the patient is having difficulty with the setup. For example, such a special message may include contact information for customer support or a voice activated menu of different languages the instructions may be given in that the patient may select from.

Standard voice messages or alarms delivered prior to or during the delivery of treatment may be customized for a patient. The standard alarms may also be modified so that a speaker or other audio device provides audio output in a language the patient understands (e.g., Spanish, English, French, German, etc.). Additionally, the messages may be customized to include the name of the patient to personalize the instructions.

The audio input and outputs provided by the defibrillator may be created or modified during a setup phase conducted during an initial use of the defibrillator by a patient. Such a setup phase may be used to determine the language all audio output should be spoken in and permit the name of the patient to be learned by the processing unit or stored in memory connected to the processing unit. The processing unit 15 may also be configured so that the patient's voice signature is identified and saved in a storage device, such as, for example, memory in the processing unit 15 or memory operatively connected to the processing unit 15.

The processing unit 15 can also be configured to generate a unique identifier that is related to the patient. Such an identifier may be used to determine who the patient is or the patient that is assigned to wear the defibrillator. Features from the patient's voice signature or saved voice recordings can be used to create the identifier. Such an identifier may be created as part of the setup phase.

Facilities that have multiple patients that are required to wear defibrillators may need a method of determining which patient is assigned to wear a particular defibrillator so the facility can ensure the proper defibrillator is worn by the proper patient. A recording of the patient's name may be stored in memory contained within the processing unit 15, operatively connected to the processing unit 15 or otherwise stored by the processing unit 15. The name of the patient may then be identified by an audio message sent by a speaker or other audio device 16 to identify the intended user of the device. The processing unit 15 may be configured so the audio device 16 provides such output whenever the device is activated or upon the activation of an actuator operatively connected to the processing unit 15, such as, for example, a button on the monitor 15 or an actuator operatively connected to the processing unit 15. The processing unit 15 may also be configured so a verbal command received from an audio device 16, such as, for example, a microphone, may cause the patient's name to be output provided by an audio device 16, such as, for example, a speaker.

Figure 2:
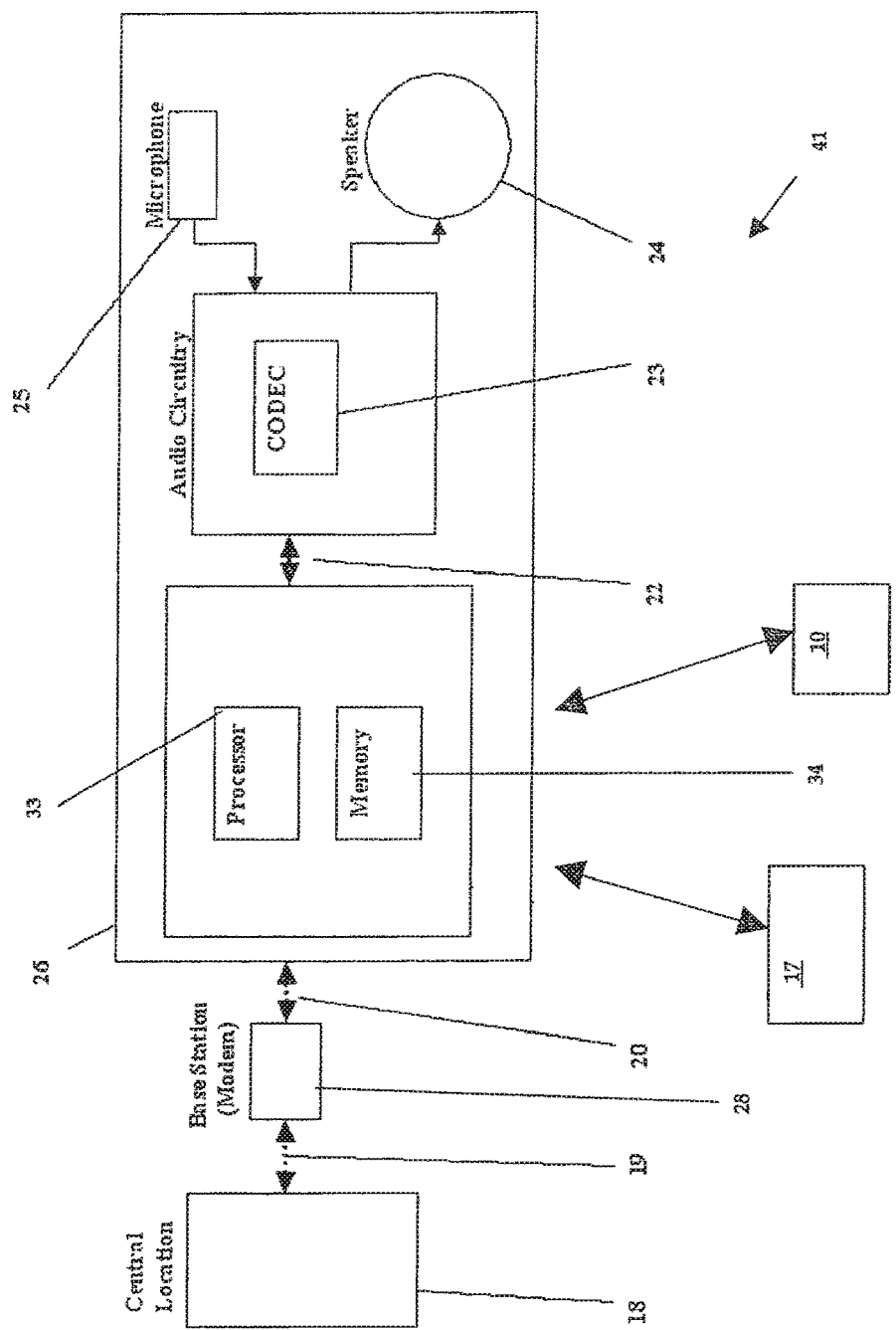
FIG. 2 is a block diagram of an embodiment of the present invention that illustrates a system that includes an embodiment of a wearable defibrillator configured to interact with a base station and a central location.

Referring to FIG. 2, a wearable defibrillator 41 is typically incorporated into a system to provide treatment to a patient. The system may include a wearable defibrillator 41 that has a processor 33 operatively connected to memory 34, a microphone 25, a speaker 24, one or more therapy pads 17, one or more electrodes 10 and a base station 28 that includes one or more networking or communication devices such as, for example, a modem or other networking device configured to connect the processor 33 or defibrillator 41 to other devices such as, for example, a computer or server or other central location 18. The processor 33, memory 34, speaker 24 and microphone 25 may be housed within a processing unit 26 along with audio circuitry that includes, for example, a CODEC 23. In some embodiments, one or more communication devices such as, for example, a modem, network card, networking programs, other networking mechanisms or any combination thereof may be connected to or incorporated into the processing unit 26 such that the processor 33 of the processing unit 26 is configured to cause one or more of the communication devices to connect the wearable defibrillator 41 to the central location 18. The central location 18 may include an apparatus operated by a hospital or other care monitoring entity that is configured to store patient related data transmitted to the central location 18. The central location 18 may also be configured to oversee or manage at least a portion of the operation of one or more wearable defibrillators 41.

The processor 33 may be configured so the patient may communicate with customer support personnel that are able to operatively connect to the central location 18. The patient may communicate with such personnel using the microphone 25 and speaker 24. The base station 28 is operatively connected with the processor 33 by a connection 20, which may be a wireless connection or a wired connection such as, for example, a USB connection. The base station 28 may include a wireless or wired modem or other transceiver that is preferably configured to establish a link 19 to the central location 18 that permits the microphone 25 to send input received from the patient to the central location 18 so that service or support representatives may receive the information. The processor 33, base station 28 and central location 18 are also configured so the speaker 24 may relay output obtained from the central location 18. Such communications may be transmitted to and from the central location 18 by transceivers, modems or other devices operatively connected to the central location 18, base station 28 and/or processor 33. The base station 28 or processing unit 26 may be configured to encrypt data transmitted to the central location 18 so that any unsecured network (e.g., cellular, wireless, POTS, etc.) available to a patient can be used.

The communications obtained from the central location 18 may include feedback from personnel connected to the central location 18. The base station 28 and processor 33 may also be configured so the patient may communicate with emergency medical support personnel attempting to help the patient or to report problems with the defibrillator to medical support staff or the manufacturer of the defibrillator. Such staff may be connected to the central location 18 or may be available for communication through other means such as, for example, cellular phone connections or other communication apparatuses.

The central location 18 may include one or more computers, servers, and programs or other software that are configured to send survey questions or other queries to one or more patients. Such queries can include questions regarding a patient's health or the condition of the defibrillator. The processor 33 may also be configured so the speaker 24 asks survey questions that are stored in the memory 34 so that periodic responses from the patient can be recorded and stored in the memory 34, in the central location 18 or a device connected to the central location 18. Such saved responses may be periodically updated and tracked to verify the patient is not experiencing any symptoms indicating increased risk of experiencing a condition that may require treatment. Changes in the patient's voice may also be stored and tracked to determine changes in breathing characteristics as an additional symptom that may be pertinent to a change in the patient's condition or diagnosis.

Examples of survey questions or periodic condition status questions may include: Are your legs swelling?; Are you having breathing difficulties?; Have you experienced a gain in weight?; and Are you sitting up to sleep? Of course, various other questions relating to symptoms of health conditions may also be used in addition to or in place of such survey questions.

The microphone 25 and processor 33 can be configured to verify that the base station 28 is connected to the central location 18 by recording a modem speaker audio or other audio that may be produced by the portion or device of the base station 28 that is configured to connect the defibrillator 41 to the central location 18. The tones of the audio produced by the base station 28 when trying to connect the defibrillator 41 to the central location 18 can be analyzed by the processor 33 to determine if the modem is attempting a connection. For instance, such an analysis may be performed by comparing the audio input received by the microphone 25 with tone data stored in the memory 34.

The microphone 25 may also be used to verify that certain internal components are operating correctly by analyzing noise associated with activation or deactivation of mechanical components of the wearable defibrillator such as, for example, relays or switches. Correlation of the activation of the components with recorded audio may verify the functionality of the components.

For example, it can be predetermined that during a particular event, certain relays are activated at certain times. Such data can be stored in memory 34. The processor 33 can be configured to use amplitude and other audio input provided by the microphone 25 and time measurements to verify that the correct relays are activated at the correct times.

The processor 33 may be configured to cause a self-diagnostic test to be run whenever audio input is received that indicates the wearable defibrillator 41 may have been damaged. Such audio input may include high amplitude and short duration noise. Such noise may be equivalent or similar to noise produced from an object such as, for example, a wall, a floor, a chair or a door banging against a portion of the wearable defibrillator or when the defibrillator is dropped onto a hard surface.

The processor 33 may be configured to cause a system test to be run to verify that the wearable defibrillator 41 is functioning properly. For example, the processor 33 may cause an alarm to be emitted by the speaker 24 at different frequencies and volumes and verify the alarm is being emitted at the different volumes and frequencies by comparing the expected audio output of the speaker with the audio input received by the microphone 25. If an alarm is found to not function properly, the processor 33 may be configured to operatively connect to the central location 18 and report the problem to the central location 18 or to schedule servicing of the wearable defibrillator 41. The processor 33 may operatively connect to the central location 18 by interacting with the base station 28, as discussed above.

It should be appreciated that service personnel may review the results of the diagnostic tests and evaluate the results to determine if the wearable defibrillator needs servicing. While certain present preferred embodiments of the wearable defibrillator and certain embodiments of methods of practicing the same have been shown and described, it is to be distinctly understood that the invention is not limited thereto but may be otherwise variously embodied and practiced within the scope of the following claims.

What is claimed is:

1. An external monitoring medical device, comprising:
at least one sensor configured to be removably attached to a patient and to sense data indicative of a cardiac condition of the patient;
an operator interface device;
an output device disposed in the operator interface device of the external monitoring medical device and configured to provide one or more output to the patient; and
at least one processor disposed in the external monitoring medical device, the at least one processor configured to cause the output device to provide the one or more output to the patient in a predetermined language of the patient;
wherein the external monitoring medical device can be worn by the patient.

2. The external monitoring medical device of claim 1, wherein the external monitoring medical device comprises a wearable defibrillator.

3. The external monitoring medical device of claim 1, wherein the predetermined language of the patient comprises at least one of Spanish, English, French, and German.

4. The external monitoring medical device of claim 1, wherein the external monitoring medical device is configured to be customized for the patient.

5. The external monitoring medical device of claim 1, wherein the external monitoring medical device is configured to display a name of the patient.

6. The external monitoring medical device of claim 3, wherein the external monitoring medical device is configured to customize one or more messages to include the name of the patient to personalize instructions.

7. The external monitoring medical device of claim 1, wherein the at least one processor is configured to cause a menu of different languages in which the one or more output to the patient can be provided.

8. The external monitoring medical device of claim 7, wherein the processor is configured to allow the patient to select from the menu of different languages the predetermined language of the patient.

9. The external monitoring medical device of claim 1, wherein the output device comprises an audio output device, and the one or more output to the patient comprises an audio output in the predetermined language of the patient.

10. The external monitoring medical device of claim 1, wherein the one or more output to the patient comprises an instruction to the patient.

11. The external monitoring medical device of claim 1, wherein the at least one sensor comprises a plurality of electrodes that are removably attached to the patient.

12. The external monitoring medical device of claim 1, wherein the external monitoring medical device is configured to provide an alarm to the patient, wherein the alarm comprises one or more of a tactile simulation alarm, a visual alarm, an audio alarm, and a voice alarm.

13. The external monitoring medical device of claim 1, wherein the external monitoring medical device is configured to allow the patient to indicate whether the patient is experiencing one or more symptoms.

14. The external monitoring medical device of claim 1, wherein the at least one processor is configured to allow the patient to configure the external monitoring medical device during a setup period prior to use of the external monitoring medical device.

15. The external monitoring medical device of claim 1, further comprising a wireless communications device configured to communicate the data indicative of the cardiac condition of the patient between the external monitoring medical device and at least one of a health care provider, emergency medical support personnel, and customer support personnel.

16. The external monitoring medical device of claim 15, wherein the wireless communications device is configured to communicate with the at least one of the health care provider, the emergency medical support personnel, and the customer support personnel via a base station.

17. The external monitoring medical device of claim 15, wherein the wireless communications device is configured to send the data indicative of the cardiac condition of the patient to the at least one of the health care provider, the emergency medical support personnel, and the customer support personnel.

18. The external monitoring medical device of claim 15, wherein the wireless communications device is configured to receive the one or more output to the patient from the at least one of the health care provider, the emergency medical support personnel, and the customer support personnel.

19. The external monitoring medical device of claim 1, wherein the one or more output to the patient comprises at least one survey question regarding at least one of a health of the patient and a condition of the external monitoring medical device.

20. An external monitoring medical device, comprising:
a plurality of ECG sensing electrodes configured to be removably attached to a patient and to detect one or more ECG signals of the patient;
sensor circuitry operationally coupled to the plurality of ECG electrodes, the sensor circuitry configured to sense data indicative of a cardiac condition of the patient based on the one or more ECG signals of the patient;
an operator interface device;
an output device disposed in the operator interface device of the external monitoring medical device and configured to provide one or more output to the patient;
at least one processor disposed in the external monitoring medical device, the at least one processor configured to
cause the output device to provide the one or more output to the patient in a predetermined language of the patient; and
cause the output device to customize the one or more output to the patient, including outputting the name of patient via the output device;
wherein the external monitoring medical device can be worn by the patient.

21. The external monitoring medical device of claim 20, wherein the external monitoring medical device comprises a wearable defibrillator.

22. The external monitoring medical device of claim 20, further comprising a wireless communications device configured to communicate the data indicative of the cardiac condition of the patient between the external monitoring medical device and at least one of a health care provider, emergency medical support personnel, and customer support personnel.

23. The external monitoring medical device of claim 22, wherein the wireless communications device is configured to communicate with the at least one of the health care provider, the emergency medical support personnel, and the customer support personnel via a base station.

24. The external monitoring medical device of claim 22, wherein the wireless communications device is configured to send the data indicative of the cardiac condition of the patient to the at least one of the health care provider, the emergency medical support personnel, and the customer support personnel.

25. The external monitoring medical device of claim 22, wherein the wireless communications device is configured to receive the one or more output to the patient from the at least one of the health care provider, the emergency medical support personnel, and the customer support personnel.

26. The external monitoring medical device of claim 22, wherein one or more output to the patient comprises at least one survey question regarding at least one of a health of the patient and a condition of the external monitoring medical device.

27. A method for monitoring a patient by an external monitoring medical device worn by the patient, comprising:
detecting one or more ECG signals of the patient via a plurality of ECG sensing electrodes configured to be removably attached to the patient and coupled to the external monitoring medical device;
sensing data indicative of a cardiac condition of the patient at the external monitoring medical device based on the detected one or more ECG signals of the patient;
causing an output device disposed in the external monitoring medical device to provide one or more output to the patient, wherein the one or more output is configured to be provided in a predetermined language of the patient; and
causing the output device to customize the one or more output to the patient, wherein the customization comprises outputting the name of patient via the output device.

28. The method of claim 27, wherein the external monitoring medical device comprises a wearable defibrillator.

29. The method of claim 27, further comprising communicating the data indicative of the cardiac condition of the patient from the external monitoring medical device to a server.

* * * * *

UNITED STATES PATENT AND TRADEMARK OFFICE
CERTIFICATE OF CORRECTION

PATENT NO. : 10,004,893 B2  
APPLICATION NO. : 15/468196  
DATED : June 26, 2018  
INVENTOR(S) : John D. Macho et al.

Page 1 of 1

It is certified that error appears in the above-identified patent and that said Letters Patent is hereby corrected as shown below:

On the Title Page

Item (Notice), Line 3, delete the second occurrence of "days."

In the Specification

Column 5, Line 59, delete "electrocardiograms.", insert -- electrocardiograms --

Signed and Sealed this  
Twenty-seventh Day of November, 2018

Andrei Iancu  
*Director of the United States Patent and Trademark Office*